(12) United States Patent
Haeberli et al.

(10) Patent No.: US 6,288,533 B1
(45) Date of Patent: Sep. 11, 2001

(54) METHOD AND APPARATUS FOR DETECTING ROTOR POSITION BY USE OF MAGNETIC FIELD SENSOR PAIRS

(75) Inventors: Andreas Haeberli, Campbell, CA (US); Christoph Maier, Oberengstringen; Matthias Metz, Zürich, both of (CH)

(73) Assignee: Physical Electronics Laboratory, Zurich (CH)

( * ) Notice: Subject to any disclaimer, the term of this patent is extended or adjusted under 35 U.S.C. 154(b) by 0 days.

(21) Appl. No.: 09/230,427

(22) PCT Filed: May 28, 1998

(86) PCT No.: PCT/EP98/03149
§ 371 Date: Apr. 1, 1999
§ 102(e) Date: Apr. 1, 1999

(87) PCT Pub. No.: WO98/54547
PCT Pub. Date: Dec. 3, 1998

Related U.S. Application Data
(60) Provisional application No. 60/047,905, filed on May 29, 1997.

(51) Int. Cl.[7] .............................. G01B 7/30; G01D 5/14
(52) U.S. Cl. .................. 324/207.2; 324/207.12; 324/207.25
(58) Field of Search ................ 324/207.12, 207.2, 324/207.21, 207.25, 173, 174

(56) References Cited

U.S. PATENT DOCUMENTS

| | | | |
|---|---|---|---|
| 4,283,679 | * 8/1981 | Ito et al. | 324/207.25 X |
| 4,490,674 | * 12/1984 | Ito | 327/207.25 |
| 5,055,781 | * 10/1991 | Sakakibara et al. | 324/207.25 X |
| 5,148,106 | * 9/1992 | Ozawa | 324/207.25 X |
| 5,861,747 | * 1/1999 | Kubinski | 324/207.21 |

FOREIGN PATENT DOCUMENTS

| | | |
|---|---|---|
| 38 26 408 | 2/1989 | (DE) . |
| 2 143 328 | 2/1985 | (GB) . |

* cited by examiner

Primary Examiner—Gerard R. Strecker
(74) Attorney, Agent, or Firm—Oppedahl & Larson LLP

(57) ABSTRACT

The rotation position of a rotor (2) rotatable around a rotation axis (1) is determined by mounting a magnetic source (2.1) on the rotor, by providing on a stator (3) at least three sensors (4, 5, 6, 7) for measuring the magnetic field of the magnetic source and being arranged in at least two pairs (4/5, 6/7), calculating the difference of quantities measured by the two sensors of each sensor pair, calculating the ratio of the difference values of two pairs and comparing the ratio with a predetermined function of said ratio versus the rotation position. This rotation position determination is very robust against offset and sensitivity variations common to all sensors (4, 5, 6, 7) and against external magnetic fields and can easily be made robust against mechanical tolerances between rotating and stationary parts also. In a preferred embodiment, there are four sensors (4, 5, 6, 7) arranged at the corners of a square perpendicular to and symmetrical relative to the rotation axis (1). The sensors (4, 5, 6, 7) are advantageously Hall sensors integrated together with read-out and calculation electronics in one die.

15 Claims, 2 Drawing Sheets

METHOD AND APPARATUS FOR DETECTING ROTOR POSITION BY USE OF MAGNETIC FIELD SENSOR PAIRS

This application claims priority from U.S. application Ser. No. 60/047,905 filed May 29, 1997.

FIELD OF THE INVENTION

The invention is in the field of contactless angle measurement. It concerns a method and an apparatus for detecting the rotation position of a rotor with the aid of a magnetic source connected to the rotor and of stationary sensor means for measuring the magnetic field of the magnetic source. The method and arrangement according to the invention are applicable e.g. for rotary switches or for rotary position detection.

BACKGROUND OF THE INVENTION

The measurement of rotation angle is required in various applications, such as manual electrical switches or position detection of a motor. Depending on cost and accuracy constraints, this task can be accomplished by various methods, such as mechanical contacts, optical encoders, or magnetic encoders. Modern integrated circuit technology offers the possibility to integrate magnetic sensors and their readout and angle calculation electronics on one die. This allows embodiments of detectors of mechanical rotation which consist of a permanent magnet attached to the rotor and monolithically integrated sensor means attached to a stator, at competitive cost, yet good performance. The absence of mechanical contact between the rotor with the magnet and the stator with the sensor means allows for hermetic encapsulation of the sensor means. This permits wear free angle measurements under harsh environmental conditions.

The robustness of the angle measurement against mechanical tolerances, against device variation, and against external electromagnetic fields, while keeping fabrication cost low, is a major performance criterion.

SUMMARY OF THE INVENTION

An object of the invention is to show a method and to create an arrangement for detecting the rotation position of a rotor using a magnetic source connected to the rotor and stationary magnetic field sensor means for measuring the magnetic field of the magnetic source, which method and arrangement allow, compared to known such methods and arrangements, increased robustness against sensitivity and offset variations of the sensor means, against external magnetic fields and furthermore against mechanical tolerances regarding the relative positions of the sensor means and the magnetic source.

The inventive arrangement for contactless angle measurement comprises a magnetic source mounted to the rotating part (rotor) rotatable around a rotation axis and an array of magnetic sensors mounted on the non-rotating part (stator). The magnetic source is arranged such that the magnetic field has no rotational symmetry relative to the rotation axis. The sensor means consists of at least three sensors arranged in at least two sensor pairs, whereby each sensor may be replaced by a cluster of sensors (plurality of sensors arranged very close to each other). The sensors, e.g. Hall sensors, are arranged in such a way that at least the two sensors of each sensor pair are sensitive to parallel components of the magnetic field. Furthermore, the sensors are such arranged that connecting lines each connecting two sensors of one sensor pair have projections in a plane perpendicular to the rotation axis which are angled relative to each other. Advantageously, the sensors of each pair are positioned in one plane perpendicular to the rotation axis, e.g. all pairs in the same plane.

According to the inventive method, the mechanical angle (rotation position of the rotor) is determined by calculating at least one ratio of two differential signals of one sensor pair each (the differential signal of a sensor pair being the difference between the signals of the two sensors of the pair) and by comparing the calculated ratio with a predetermined (calculated or experimentally determined) function of said ratio versus the rotation angle. If instead of single sensors clusters of sensors are used it is the mean value of the sensor signals of the cluster which is used for calculating the differential signals.

This method yields an angle determination which is insensitive to variations common to the two sensors of each pair (e.g. offset) and to sensitivity variations common to all sensors contributing to one ratio, as well as to external magnetic fields.

For reducing or even suppressing the influence of mechanical misalignment of the rotating magnetic source and the sensor array with respect to each other and to the rotation axis, the magnetic source and the sensor array are such designed and such arranged that the magnetic field component to be measured at any possible sensor location is described by the product of a first order polynomial within a planar surface substantially perpendicular to the rotation axis (magnetic field changing linearly within such a planar surface, i.e. having no curvature), and a function perpendicular to said planar surface, which function is essentially the same for all sensor locations and is advantageously well approximated by a linear function.

In addition to providing information about the angle of mechanical rotation, the field of the magnetic source can be used to hold the rotor in place by adding a ferromagnetic yoke to the stator. Said yoke, shaping the magnetic field of the rotor, further enhances the insensitivity of the device against mechanical misalignment.

BRIEF DESCRIPTION OF THE DRAWINGS

The invention is described in more detail referring to the following Figures, wherein.

DESCRIPTION OF THE PREFERRED EMBODIMENTS

Figure 1:
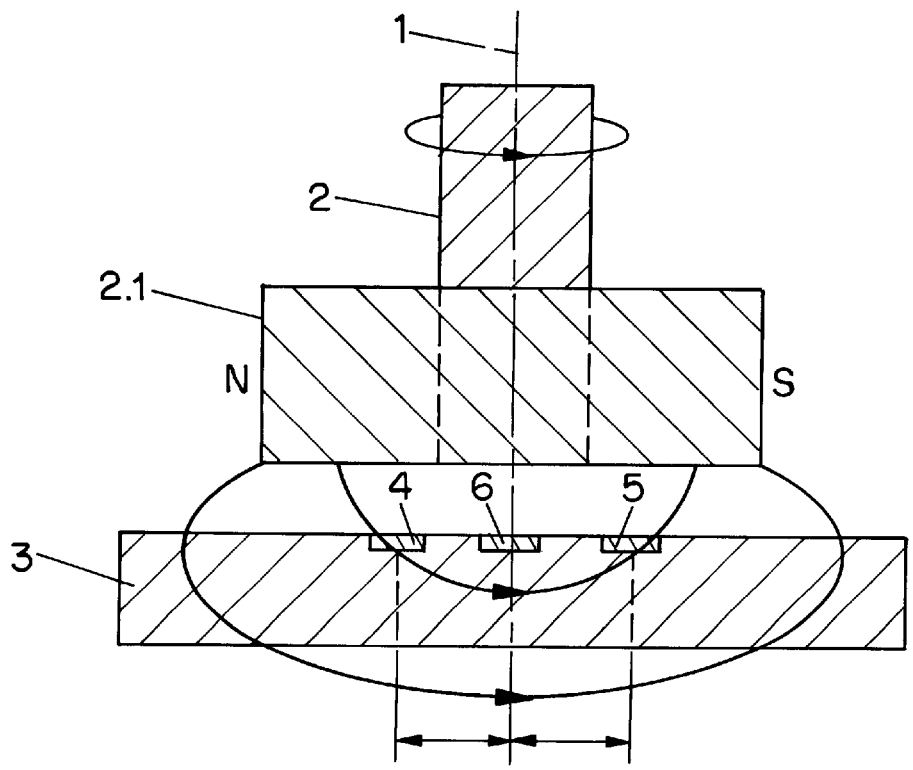
FIG. 1 shows a diagrammatic cross-sectional view of an exemplary embodiment of the inventive arrangement for determining the rotation position of a rotor 2 rotatable around a rotation axis 1, the arrangement comprising a rotor 2 containing a magnetic source 2.1, and a stator 3 with a planar array of Hall devices 4, 5 and 6 (fourth hall device not visible), e.g. monolithically integrated with signal conditioning and angle calculation electronics on an integrated circuit.

A preferred embodiment of the inventive arrangement is illustrated in FIG. 1 (section along rotation axis 1). The arrangement comprises a magnetic source 2.1 attached to a rotor 2 rotating about an axis 1 and an array of e.g four magnetic field sensors attached to a stator 3 (three sensors 4, 5 and 6 visible). The sensors are located within the field of the magnetic source. The field sensors are sensitive to the magnetic field or to a particular component thereof, to be denoted as $B_\perp$. The field sensors are e.g. Hall sensors being sensitive to the component of the magnetic field perpendicular to their sensor plane and they are integrated in one die preferably together with readout and angle calculation electronics.

Figure 2:
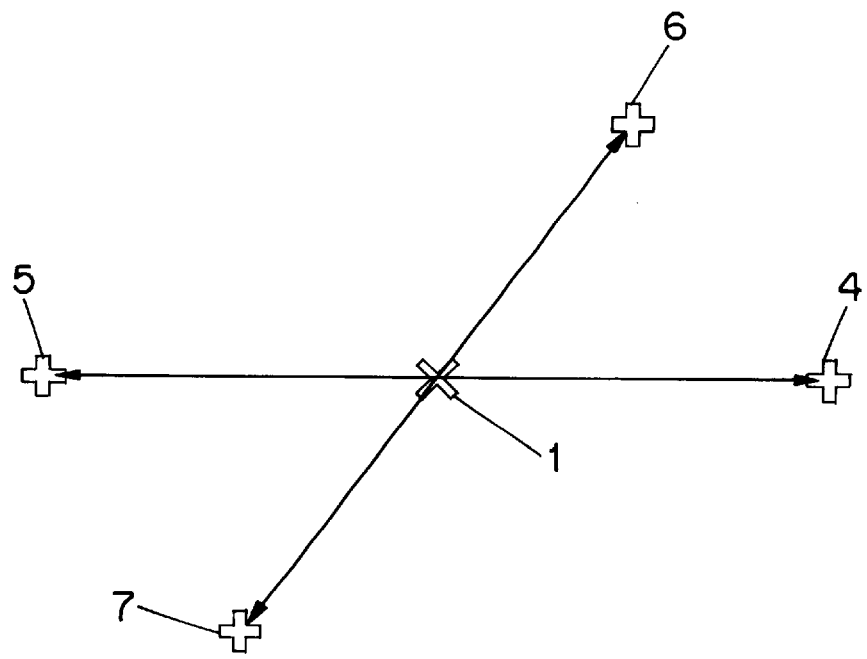
FIG. 2 shows an exemplary array of two sensor pairs 4/5 and 6/7 as seen along the axis of rotation 1, wherein each sensor pair is essentially located within a plane perpendicular to the axis of rotation 1 and wherein both pairs may but need not share the same plane.

As shown in FIG. 2 (top view), the exemplary sensor array comprises two pairs of sensors 4/5 and 6/7, preferably located within one plane, which plane is oriented substantially perpendicular to the rotation axis 1 of the rotor 2. The connecting lines between the two sensors of each pair must not all be parallel. It is possible that different sensor pairs share one common sensor (e.g in an array with three sensors only).

The signal measured by each sensor is proportional to $B_\perp$ at the sensor location. For each pair of sensors, the difference of the two sensor signals is generated. The angle of rotation, to be denoted as $\Phi$, is calculated as a function of a ratio of difference signals. This method is insensitive to multiplication of the sensor signals with a factor common to all sensors whose measured signals are utilized for calculating one ratio of differences, as well as to the addition of a signal common to a pair of sensors, for instance due to sensor offset or external magnetic fields. An ambiguity of angle $\Phi$ of $\pm 180°$ introduced by using said method to determine the angle is eliminated by utilizing a plurality of ratios of differences to determine the angle, or by evaluating the sign of the difference signals of at least one of the sensor pairs, i.e. evaluating the difference signal as a positive or a negative value.

One preferred embodiment of a sensor array for an inventive arrangement comprises two pairs of sensors, the sensors of each pair being located at opposing corners of a square which square is arranged perpendicular to and symmetrical with respect to the rotation axis 1 of the rotor 2, whereby all sensors measure parallel components of the field, e.g. components perpendicular to the plane of the square. In this particular case, the mechanical angle $\Phi$ is given by:

$$\Phi = \arctan\{(S_7 - S_6)/(S_5 - S_4)\} = \text{arc cot}\{(S_5 - S_4)/(S_7 - S_6)\}.$$

More sensor pairs can be added for improved accuracy.

Low cross-sensitivity of the measured rotation angle $\Phi$ determined by the inventive method to mechanical translation of the magnetic source and/or the sensor array with respect to each other and to the axis of rotation is achieved by designing the inventive arrangement such that in the vicinity of each possible sensor location, the magnetic field is linear within the plane in which the sensors are arranged, and such that at each possible sensor location the change of the magnetic field parallel to the rotation axis is governed by substantially the same function.

The measures as indicated above for substantially suppressing the effect of translation are explained as follows: Let $V_i$ denote the volume in a rotating coordinate frame attached to the magnetic source which encloses the position of both field sensors of one sensor pair, labeled by i, for any rotational angle $\Phi$ and any mechanical displacement that may occur under permitted operating conditions of the angle detector. Let x and y denote rectilinear coordinates perpendicular to the axis of rotation, z the linear coordinate parallel to the axis of rotation. The field component of the magnetic source measured by the sensors within the volume $V_i$ is essentially described by a function $B_\perp(x,y,z) = B_i^0 + a_i \cdot x \cdot f_i(z)$, with constants $B_i^0$ and $a_i$ and function $f_i(z)$ independent of x and y. The functions $f_i(z)$ and $f_j(z)$, associated to sensor pairs i and j whereof the ratio of differences is calculated to determine the angle $\Phi$ are essentially equal. Mechanical translation of the sensor array or the magnetic source perpendicular to the axis of rotation results in a common mode signal of sensor pairs, which is substantially cancelled by utilizing difference signals. Mechanical translation of the sensor array or the magnetic source parallel to the axis of rotation (i. e. a change in distance between magnetic source and sensor array) does not influence the measured angle $\Phi$ as the ratio of two differential signals remains essentially unchanged with z due to the condition on the set of $f_i(z)$ functions stated above.

For achieving low sensitivity or even insensitivity against tilt, i.e. mechanical rotation of the magnetic source and/or the sensor array about an axis (axis of tilt) perpendicular to the rotation axis, the inventive arrangement is designed such that in the vicinity of each possible sensor location, the change of the magnetic field parallel to the rotation axis is governed by substantially the same linear function and the sensors of each pair are arranged such that the connecting lines connecting two sensors of one pair are perpendicular to the rotation axis and are intersected by the rotation axis in their middle.

The measures as indicated above for substantially suppressing the effect of tilt are explained as follows: To first order in mechanical displacement, tilt of the sensor array or the permanent magnet with respect to the predetermined axis of rotation results in a common mode signal of sensor pairs if the sensors forming a pair are essentially located on the intersection of a plane perpendicular to the axis of rotation and the surface of a cylinder centered at the axis of tilt. For practical occurrences of tilt, namely play of the rotor about some bearing point or tilted mounting of the sensor array, or of the magnetic source with respect to the axis of rotation, the axis of tilt and the axis of rotation can be assumed to intersect each other in a point. Consequently, influence of tilt on the measured angle is largely rejected by using difference signals of sensor pairs if the sensors forming a pair are substantially located within a plane perpendicular to the axis of rotation, such that the axis of rotation intersects said plane in the center of each line connecting two sensors of one pair. The better the functions $f_i(z)$ are approximated by their first order Taylor expansion around the nominal positions of the sensors, the better is the rejection of tilt on the measured angle.

Figure 3:
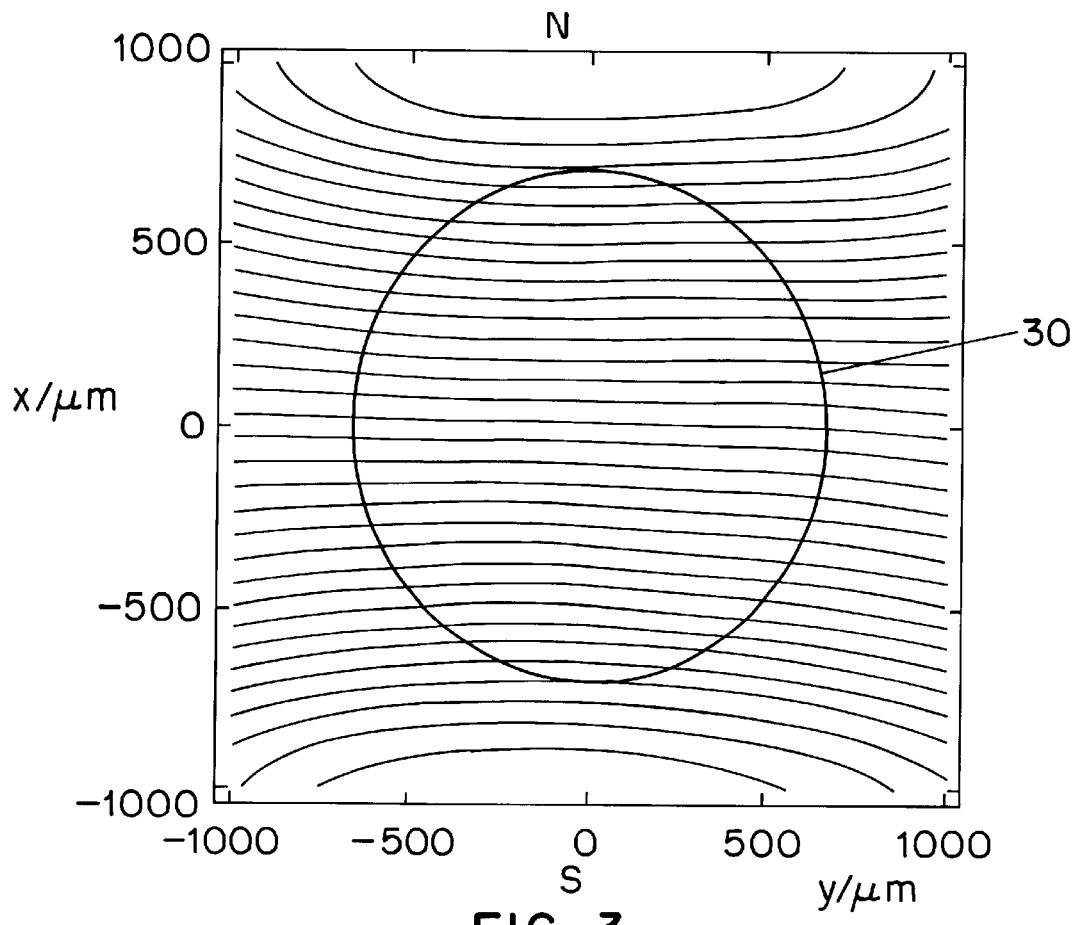
FIG. 3 shows the magnetic field component parallel to the axis of rotation (lines of equal field strength in square of 2×2 mm centered between north and south pole), as generated by a bar magnet, at a distance of some 0.5 mm from the surface of the magnet, whereby the region enclosed in the circle 30 (area of about 120 µm diameter) complies to the requirements as given for robustness against mechanical tolerances.

In an exemplified embodiment, a homogeneously magnetized bar magnet, which has the shape of a cuboid of 2 mm×3 mm×3 mm, the first dimension being the distance between the two pole faces, produces a field component which substantially fulfills the conditions as named above for optimum rejection of sensor offset and sensitivity variations as well as for mechanical tolerances in a volume of $(0.6 \text{ mm})^3$, located some 0.5 mm from one of the rectangular surfaces of the magnet. FIG. 3 shows the lines of equal magnetic strength of the magnetic field created by the magnet as described above at a distance of 0.5 mm from one of the rectangular surfaces of the magnet. The area shown in the Figure is a square of 2 mn (2×100 μm) in the center of the rectangular surface, the north/south axis being oriented top/bottom in the Figure. The middle region of this area enclosed by the circle 30 fulfills the conditions as given above.

In the exemplified embodiment of the inventive arrangement the cuboid magnet is mounted on the rotor such that the rotation axis is parallel to the pole faces of the magnet and runs through the center points of two opposite rectangular surfaces of the magnet and the sensors are arranged e.g. in a square which is oriented perpendicular to the rotation axis, which is distanced from the rectangular surface of the magnet by approximately 0.5 mm and in which the sensors of one pair are distanced from each other by not more than approximately 1 mm (positioned within the circle 30 indicated in FIG. 3).

Figure 4:
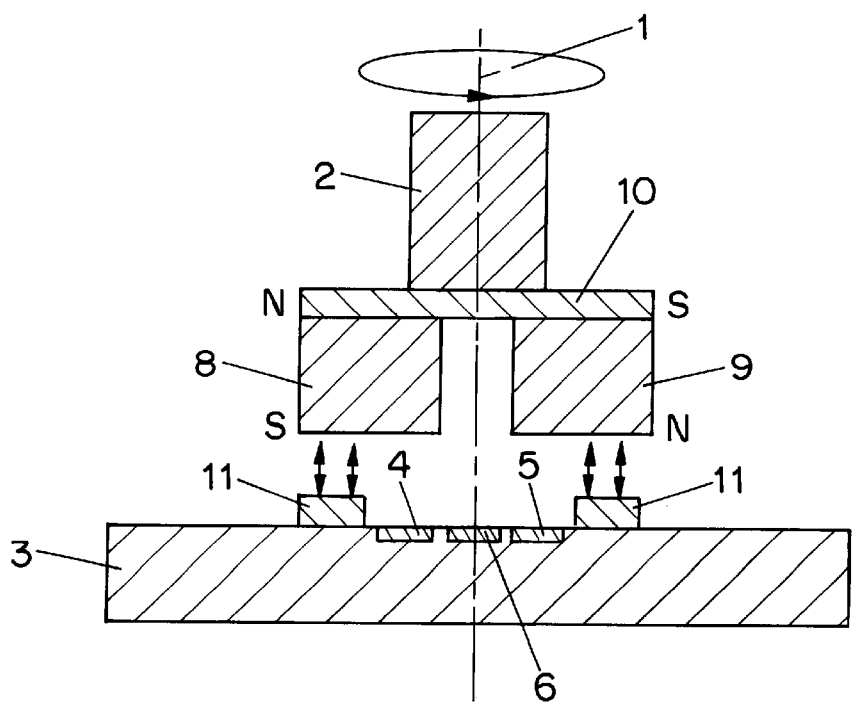
FIG. 4 shows a cross section of a further exemplary embodiment of the inventive arrangement for measuring the angle of mechanical rotation about an axis 1, the arrangement comprising a rotor 2 with two bar magnets 8 and 9 and a ferromagnetic yoke 10 and a stator 3 with an array of Hall sensors 4, 5, 6 and a ferromagnetic yoke 11, whereby the ferromagnetic yoke 11 serves for holding the rotor 2 in place and for shaping the magnetic field in the vicinity of the sensors.

FIG. 4 shows a further exemplified embodiment of the inventive arrangement. In this embodiment, the stator 3 comprises in addition to the sensor array with visible sensors 4, 5 and 6, a ferromagnetic yoke 11 having the form of a ring within which the sensors are positioned. The yoke 11 fulfills the dual purpose of holding the rotor 2 in place and of shaping the magnetic field of the rotating magnetic source to attain a volume V for locating the sensors in which volume the measured magnetic field component $B_\perp$ complies to the conditions stated above. Being rigidly connected to the sensor array, the yoke 11 reduces changes of the field component $B_\perp$ within V due to movement of the rotor 2 other than rotation about the rotation axis 1.

The magnetic source according to the embodiment of FIG. 4 consists of two cuboid or cylindrical magnets 8 and 9 and of a further ferromagnetic yoke 10 or of a U-shaped permanent magnet, whereby this magnetic source has a north and a south face arranged in substantially the same plane perpendicular to the rotation axis and substantially symmetrical to the rotation axis.

What is claimed is:

1. A method for determining the rotational position of a rotor which is rotatable about an axis of rotation wherein the rotor carries a magnetic source which creates a rotationally non-symmetrical magnetic field relative to the axis of rotation, said magnetic source having two magnetic poles, and for reducing the influence of external magnetic fields and of sensitivity and offset variations of sensor means on the accuracy of the determination of rotational position, the method comprising:

providing stationary sensor means in the form of at least three sensors arranged in at least two sensor pairs so that the sensors of each sensor pair are sensitive to substantially parallel components of the magnetic field and wherein connecting lines, each connecting two sensors of one sensor pair, have projections lying in a plane perpendicular to the axis of rotation, the connecting lines lying at an angle relative to each other, the sensor means positioned at a distance from the volume between the two magnetic poles, further characterized in that the sensors of the sensor means each sense the field strength in a specific direction in a specific sensor position, measuring local components of the magnetic field using stationary sensor means, calculating differences between the quantities measured by the two sensors of each sensor pair and at least one ratio of the differences of two pairs, and determining the rotational position of the rotor by comparing the at least one ratio measured by the sensor means with a predetermined function of the field component versus the rotation position of the rotor.

2. Method according to claim 1, characterized in that for reducing the influence of mechanical translation of the stationary sensor means and/or the magnetic source relative to each other or relative to the rotation axis, the magnetic source is designed such that the magnetic field comprises a volume in which the component to be measured by the sensors varies substantially linearly in a plane perpendicular to the rotation axis and according to a function parallel to the rotation axis which function is substantially the same in all locations within said volume and the sensors are positioned in said volume such that each line connecting the two sensors of one sensor pair is substantially perpendicular to the rotation axis.

3. Method according to claim 2, characterized in that for reducing the influence of mechanical tilt of the magnetic source and/or the sensor means relative to the rotation axis, the magnetic source is such designed that within said volume the magnetic field varies substantially linearly in a direction parallel to the rotation axis and the sensors are arranged such that each line connecting the two sensors of one sensor pair is intersected by the rotation axis and divided into two equal halves.

4. Method according to claim 3, characterized in that for preventing ambiguity between rotational positions of the rotor differing by an angle of 180°, a plurality of ratios of differences for different couples of sensor pairs is calculated.

5. Method according to claim 3, characterized in that for preventing ambiguity between rotational positions of the rotor differing by an angle of 180°, the step of determining the rotation position includes calculating the differences of the measuring signals and the corresponding ratios with a positive or a negative sign.

6. An apparatus for determining the rotational position of a rotor rotatable about an axis of rotation comprising a magnetic source mounted on said rotor, the magnetic source having two magnetic poles;

a stator;

sensor means carried by said stator for measuring a magnetic field created by said magnetic source, said sensor means comprising at least three sensors in at least two sensor pairs so that sensors of each pair are sensitive to substantially parallel components of said magnetic field, and wherein lines connecting each two sensors of each pair lie in a plane perpendicular to said axis of rotation and at angles to each other, said sensor means positioned at a distance from the volume between the two magnetic poles, further characterized in that the sensors in the sensor means each sense the field strength in a specific direction in a specific sensor position; and means for calculating the differences between signals of said two sensors of each pair and for calculating a ratio of the differences for said at least two sensor pairs to determine said rotational position.

7. Arrangement according to claim 6, characterized in that at least part of the sensors are replaced by a sensor cluster consisting of a plurality of sensors arranged close to each other and in that the means for calculating comprises means for calculating a mean value of the measuring signals of the sensors of each sensor cluster.

8. Arrangement according to claim 7, characterized in that the two sensors of each sensor pair or the sensors of all sensor pairs are arranged in the same plane perpendicular to the rotation axis.

9. Arrangement according to claim 8, characterized in that the two sensors of each sensor pair are arranged such that the line connecting the two sensors intersects the rotation axis and is cut into two equal halves by the rotation axis.

10. Arrangement according to claim 7, characterized in that the sensor means comprises four sensors arranged in the corners of a square, which square is oriented perpendicular and symmetrical to the rotation axis.

11. Arrangement according to claim 10, characterized in that the sensors are Hall sensors.

12. Arrangement according to claim 11, characterized in that the sensors are integrated together with readout and calculating electronics in one die.

13. Arrangement according to claim 12, characterized in that the magnetic source is a permanent magnet having two opposite pole faces and that the magnet is arranged on the rotor such that the rotation axis goes through the center of the magnet and is parallel to the two pole faces.

14. Arrangement according to claim 12, characterized, in that the magnetic source comprises permanent magnet means with two pole faces positioned substantially in one plane and that the permanent magnet means is arranged on the rotor such that the pole faces are substantially perpendicular and substantially symmetrical to the rotation axis.

15. Arrangement according to claim 14, characterized in that the stator further comprises a stationary, ring-shaped ferromagnetic yoke and in that the sensors are arranged within the ring-shaped yoke.

* * * * *